United States Patent [19]

Gurmarnik

[11] Patent Number: 5,292,325
[45] Date of Patent: Mar. 8, 1994

[54] DEVICE FOR AND METHOD OF SUBCUTANEOUS INTRODUCTION OF A CATHETER INTO A PERIPHERAL ARTERY

[76] Inventor: Simon Gurmarnik, 38 Garrison Rd. Rt. 1, Brookline, Mass. 02146

[21] Appl. No.: 985,855

[22] Filed: Dec. 4, 1992

[51] Int. Cl.⁵ .............................................. A61B 17/00
[52] U.S. Cl. ..................... 606/108; 128/DIG. 26; 606/1
[58] Field of Search ................... 606/1, 108; 604/174, 604/178, 179; 128/DIG. 26

[56] References Cited

U.S. PATENT DOCUMENTS

| | | | |
|---|---|---|---|
| 2,727,513 | 12/1955 | Muller | 128/DIG. 26 |
| 3,568,679 | 3/1971 | Reif | 128/DIG. 26 |
| 4,516,968 | 5/1985 | Marshall et al. | 604/174 |
| 4,579,120 | 4/1986 | MacGregor | 128/DIG. 26 |
| 4,615,692 | 10/1986 | Giacalone et al. | 604/174 |
| 4,687,470 | 8/1987 | Okada | 128/DIG. 26 |
| 5,167,630 | 12/1992 | Paul | 604/174 |

Primary Examiner—Stephen C. Pellegrino
Assistant Examiner—Glenn Dawson
Attorney, Agent, or Firm—I. Zborovsky

[57] ABSTRACT

A device and a method for facilitating subcutaneous introduction of a plastic carrier includes an element having a supporting portion arranged to be supported on a skin of a patient, and a guiding portion extending substantially transversely to the supporting portion and having at least one slot formed so that when the supporting portion is placed on the skin of a patient and oriented on a surface projection line of an artery and a catheter is introduced through the slot of the guiding portion the catheter is guided on an edge formed in the guiding portion by the slot so that a tip of the catheter is introduced exactly into the artery.

1 Claim, 2 Drawing Sheets

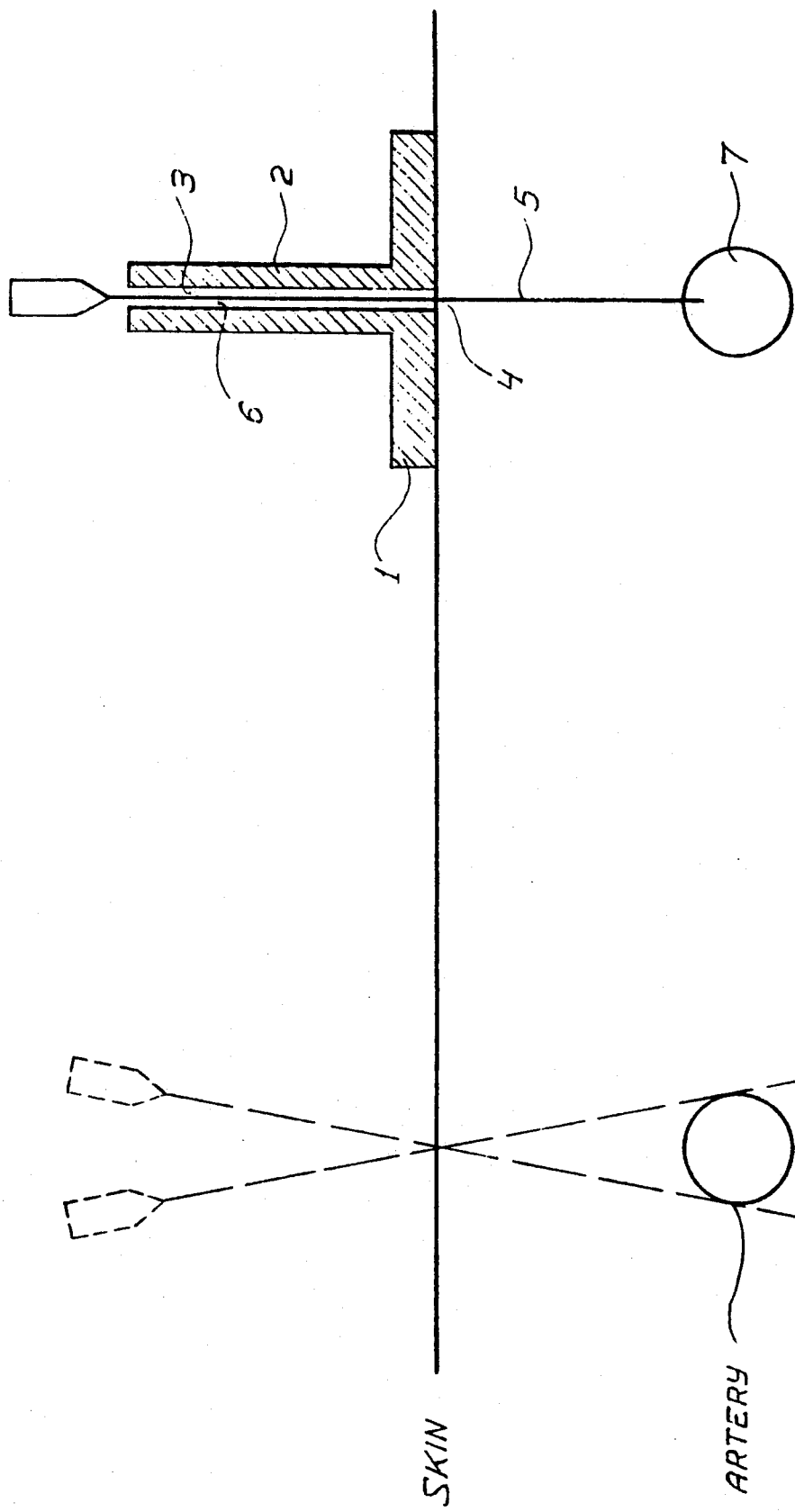

DEVICE FOR AND METHOD OF SUBCUTANEOUS INTRODUCTION OF A CATHETER INTO A PERIPHERAL ARTERY

BACKGROUND OF THE INVENTION

The present invention relates to a device and a method for facilitating subcutaneous introduction of a plastic catheter into the peripheral artery in a variety of clinical circumstances.

There is often a need to quickly catheterize a peripheral artery. This task is complicated by the fact that such arteries have small diameters and lie deep in the soft tissue. Even small errors in selection of a skin puncture point and in adjustment of an insertion angle can lead to uncertainties of the needle tip position at the artery's step greater than the artery's diameter, as shown in FIG. 1. The tip of the needle can miss the artery as shown in the drawing. This substantially decreases the success rate of catheterization and results in multiple traumatic attempts.

SUMMARY OF THE INVENTION

Accordingly, it is an object of the present invention to provide a device and a method of facilitating subcutaneous introduction of a catheter into a peripheral artery, which avoids the disadvantages of the prior art.

In keeping with these objects and with others which will become apparent hereinafter, one feature of the present invention resides, briefly stated, in a device which includes a supporting part to be supported on a skin of a patient, and a guiding part extending from the supporting part substantially transversely to the latter and having at least one slot which forms at least one guiding edge for guiding a catheter so that when said supporting portion is supported on a skin of the patient and the device is oriented relative to a projection line of an artery on the skin surface, said guiding edge guides the catheter directly into the artery.

In accordance with another feature of the present invention, a method of facilitating subcutaneous introduction of a catheter into the artery is proposed in accordance with which the above mentioned device is placed with its supporting surface on the skin of the user, and then the catheter is guided along the guiding edge into the artery upon orienting the device on a projection line of the artery on the skin.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a view showing a prior art introduction of a catheter into a peripheral artery, which results in misplacing of the catheter with missing of the artery;

FIG. 2 is a schematic view showing a cross-section of a device for facilitating subcutaneous introduction of a catheter into the peripheral artery;

DESCRIPTION OF THE PREFERRED EMBODIMENTS

Figure 3:
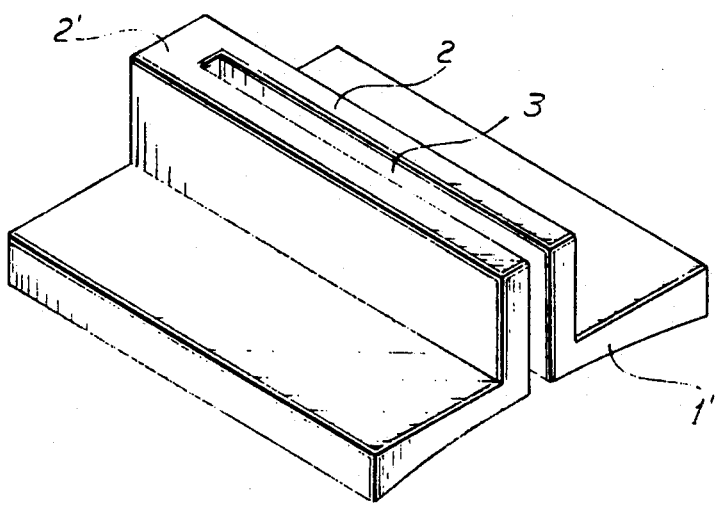
FIGS. 3-5 are perspective views showing three different modifications of the inventive device for facilitating subcutaneous introduction of a catheter into the peripheral artery.

A device for facilitating subcutaneous introduction of a catheter into a peripheral artery has a supporting portion which is identified as a whole with reference numeral 1 and formed to support the device on a skin of the user. The device further has a guiding portion 2 which extends transversely relative to the supporting portion 1. The guiding portion 2 is provided with at least one slot which is identified with reference numeral 3. The slot 3 is very narrow. For example if the needle has a diameter of 0.5 mm, the diameter of the slot can be 2.5 mm.

In order to introduce a catheter subcutaneously into a peripheral artery, the device of the invention is placed with its supporting portion 1 on the skin of a patient as shown in FIG. 2. Then a surface projection line of the artery is determined by location of the artery's pulse and marked on the skin as identified with reference numeral 4. The slot 3 of the guiding portion 2 of the device is oriented exactly on the mark on the skin. When now the needle 5 is introduced through the slot 3, a vertical edge 6 formed by the slot 3 provides guidance for the needle, so that the needle's tip is introduced exactly into the artery.

The width of the slot of approximately 2.5 mm is selected to permit easy passage of the needle 5 through it and at the same time to provide enough restraint so that the needle's tip would not miss the artery at its depth of 5–7 mm below the skin.

As can be seen from FIG. 3, the slot 3' is elongated so that it can extend along the surface projection line of the artery. The supporting portion 1' has a somewhat curved lower surface. The guiding surface 2 has a closed rear end 2' and a uniform height.

Figure 4:
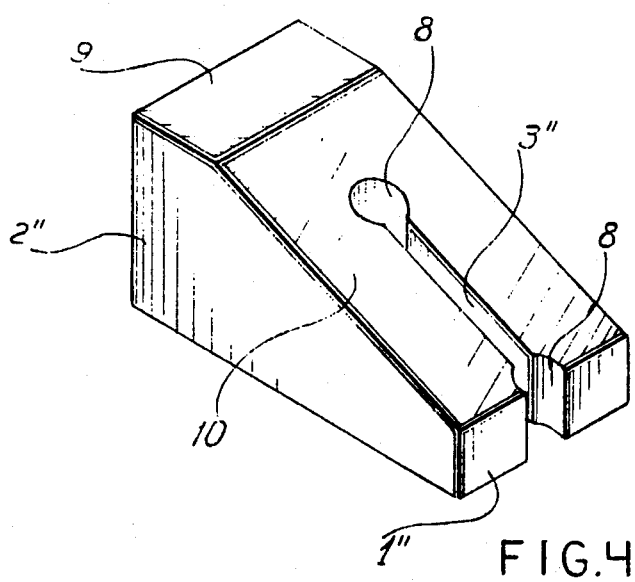

In the embodiment shown in FIG. 4, two enlarged orifices 8 are provided at the ends of the slot 3''. They permit easy location of the artery marking line on the skin. Here the supporting portion 1'' and the guiding portion 2'' have the same width. At the same time, the device has an upper surface with a portion 9 extending parallel to the lower surface and a portion 10 extending inclined relative to the lower surface.

Figure 5:
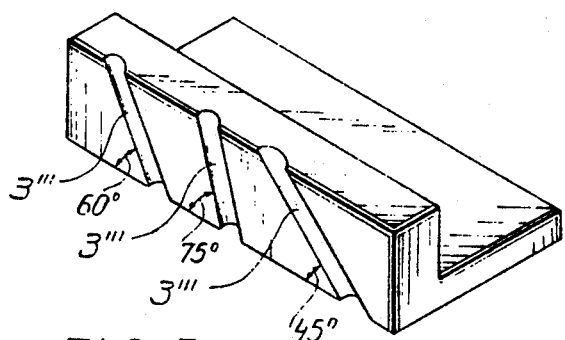

In the embodiment of FIG. 5 the slot has three individual slot portions 3''' which are inclined at several angles relative to the lower surface of the device. The needle can be introduced along any of the slots 3''' which are formed as semi-circular channels.

The device can be made of a transparent plastic material, such as for example Lucite, Plexiglass, or similar materials. It is easily sterilizable.

It will be understood that each of the elements described above, or two or more together, may also find a useful application in other types of constructions and methods differing from the types described above.

While the invention has been illustrated and described as embodied in a device and a method for facilitating subcutaneous introduction of a catheter into a peripheral artery, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A device for facilitating subcutaneous introduction of a catheter in a peripheral artery, comprising an element having a supporting portion arranged to be supported on a skin of a patient, and a guiding portion connected with said supporting portion and extending substantially transversely to said supporting portion and having at least one slot formed so that when said supporting portion is placed on the skin of the patient and oriented on a surface projecting line of an artery and a catheter is introduced through said slot of said guiding portion the catheter is guided on an edge formed in said guiding portion by said slot so that a tip of the catheter is introduced exactly into the artery, said slot having two ends each provided with an orifice having a diameter which is greater than a width of said slot, and one of said orifices being open outwardly at an edge of said element so as to facilitate easy introduction of a catheter and location of said surface projection line of the artery on the skin.

* * * * *